US009872964B2

(12) United States Patent
Cline et al.

(10) Patent No.: US 9,872,964 B2
(45) Date of Patent: Jan. 23, 2018

(54) METERED DOSE INHALER COUNTER AND METERED-DOSE INHALER INCLUDING SUCH A COUNTER

(71) Applicant: Presspart GmbH & Co. KG, Marsberg (DE)

(72) Inventors: Stephen W. Cline, Morrisville, NC (US); R. Scott Downen, Raleigh, NC (US); Karl E. Robinson, Co Durham (GB); Colin Watling, Surrey (GB)

(73) Assignee: PRESSPART GMBH & CO. KG, Marsberg (DE)

( * ) Notice: Subject to any disclaimer, the term of this patent is extended or adjusted under 35 U.S.C. 154(b) by 624 days.

(21) Appl. No.: 13/973,548

(22) Filed: Aug. 22, 2013

(65) Prior Publication Data

US 2014/0053833 A1 Feb. 27, 2014

Related U.S. Application Data

(60) Provisional application No. 61/691,991, filed on Aug. 22, 2012.

(30) Foreign Application Priority Data

Aug. 22, 2012 (GB) .................................. 1214956.3

(51) Int. Cl.
*A61M 15/00* (2006.01)
(52) U.S. Cl.
CPC ...... *A61M 15/0065* (2013.01); *A61M 15/008* (2014.02); *A61M 15/009* (2013.01); (Continued)
(58) Field of Classification Search
CPC .............. A61M 15/00; A61M 15/0065; A61M 15/009; A61M 15/008; A61M 2205/8212; (Continued)

(56) References Cited

U.S. PATENT DOCUMENTS

| 5,505,192 A | 4/1996 | Samiotes et al. |
| 5,544,647 A | 8/1996 | Jewett et al. |

(Continued)

FOREIGN PATENT DOCUMENTS

| EP | 0 775 499 | 5/1997 |
| GB | 2 405 801 | 3/2005 |

(Continued)

OTHER PUBLICATIONS

International Search Report and Written Opinion Corresponding to International Application No. PCT/US2013/056192; dated Nov. 18, 2013; 14 Pages.

(Continued)

*Primary Examiner* — Lynne Anderson
*Assistant Examiner* — Elliot S Ruddie
(74) *Attorney, Agent, or Firm* — Myers Bigel, P.A.

(57) ABSTRACT

A dose counter for a metered dose inhaler has an activation valve at a valve end of the metered dose inhaler. The dose counter includes a housing having a first end and an opposing second end. The first end receives a metered dose inhaler valve end, and the second end defines a cavity. An actuation detection assembly in the cavity includes an actuation detection element on the second end of the housing, and an activator element in the cavity of the housing. The activator element is configured to move between a first position in the cavity in which the activator element is spaced apart from the actuation detection element on the housing by a gap and a second position in which the activator element cooperates with the actuation detection element so that the actuation detection element generates an actuation signal.

24 Claims, 10 Drawing Sheets

(52) U.S. Cl.
CPC . *A61M 2205/332* (2013.01); *A61M 2205/502* (2013.01); *A61M 2205/8212* (2013.01)

(58) Field of Classification Search
CPC ........ A61M 2205/502; A61M 15/0086; A61M 15/0088; A61M 15/0091; A61M 15/08; A61M 16/0078; A61M 16/0816; A61M 16/14; A61M 16/147; A61M 2205/332; A61M 11/04; A61M 15/0068; A61M 15/0071; A61M 15/0073; A61M 15/0076; A61M 15/0081; B05B 11/0037; B05B 11/3056; B65D 83/201; B65D 83/386
USPC ............ 128/200.12, 200.14, 200.21, 200.23, 128/203.12, 203.15, 200.24, 203.28, 128/205.23

See application file for complete search history.

(56) References Cited

U.S. PATENT DOCUMENTS

| | | | |
|---|---|---|---|
| 5,622,163 | A | 4/1997 | Jewett et al. |
| 6,202,642 | B1 | 3/2001 | McKinnon et al. |
| 2003/0183226 | A1 | 10/2003 | Brand et al. |
| 2004/0255936 | A1 | 12/2004 | Urbanus |
| 2005/0028815 | A1 | 2/2005 | Deaton et al. |
| 2005/0247305 | A1* | 11/2005 | Zierenberg ........ A61M 15/0065 128/200.14 |
| 2006/0254581 | A1 | 11/2006 | Genova et al. |
| 2007/0240707 | A1 | 10/2007 | Sauzade et al. |
| 2007/0251950 | A1 | 11/2007 | Bacon |
| 2007/0295329 | A1 | 12/2007 | Lieberman et al. |
| 2009/0151721 | A1 | 6/2009 | Spaargaren et al. |
| 2010/0094099 | A1 | 4/2010 | Levy et al. |
| 2010/0250280 | A1 | 9/2010 | Sutherland |
| 2010/0252036 | A1 | 10/2010 | Sutherland et al. |
| 2011/0036346 | A1 | 2/2011 | Cohen et al. |
| 2011/0041845 | A1 | 2/2011 | Solomon et al. |
| 2011/0265788 | A1 | 11/2011 | Wu |
| 2012/0055472 | A1 | 3/2012 | Brunnberg et al. |

FOREIGN PATENT DOCUMENTS

| | | |
|---|---|---|
| GB | 2 441 597 | 9/2005 |
| GB | 2 451 833 | 2/2009 |
| JP | 2008161548 | 7/2008 |
| WO | WO 92/17231 | 10/1992 |
| WO | WO 98/56444 | 12/1998 |
| WO | WO 01/26021 | 4/2001 |
| WO | WO 01/41849 | 6/2001 |
| WO | WO 03/103759 A1 | 12/2003 |
| WO | WO 2004/039443 | 5/2004 |
| WO | WO 2004/040536 | 5/2004 |
| WO | WO 2006/126967 | 11/2006 |

OTHER PUBLICATIONS

Notification Concerning Transmittal of International Preliminary Report on Patentability in corresponding PCT Application No. PCT/US2013/056192, dated Mar. 5, 2015 (9 pages).

* cited by examiner

METERED DOSE INHALER COUNTER AND METERED-DOSE INHALER INCLUDING SUCH A COUNTER

RELATED APPLICATIONS

This application is claims priority to U.S. Provisional Application Ser. No. 61/691,991, filed Aug. 22, 2012, and European Application No. 1214956.3 filed Aug. 22, 2012, and is related to PCT Patent Application No. PCT/US2013/056192, filed Aug. 22, 2013, entitled "Dose Counter for a Metered-Dose Inhaler and Metered-Dose Inhaler Including Such a Counter", the disclosures of which are hereby incorporated by reference in their entirety.

FIELD OF THE INVENTION

The present invention relates to a metered-dose inhaler counter, to metered dose inhalers including said metered dose inhaler counter and to methods of determining when or whether said metered dose inhaler counter should be indexed.

BACKGROUND

Metered-dose inhalers (MDIs) are medication delivery devices that deliver a pharmaceutical formulation including one or more pharmaceutically active compounds ("active ingredients") to a human or other mammalian patient.

Typically the pharmaceutical formulation is delivered by the MDI as unit doses in the form of an aerosol. Each actuation of the MDI delivers one unit dose. The unit dose is expelled by the MDI and is taken into the body of the patient on inhalation, via the nose or mouth. The pharmaceutical formulation is delivered to or via the respiratory tract, notably to the lungs, of the patient on inhalation.

The MDI includes a metering valve which is configured to ensure that each dose of the pharmaceutical formulation expelled by the MDI is the same, within permitted tolerances. In particular, each dose should include the same amount of the active ingredient(s). Generally, the metering valve is configured to dispense a constant volume of the pharmaceutical formulation on each actuation of the MDI.

Metered-dose inhalers are typically used for the treatment of respiratory infections and disorders including respiratory tract infections, obstructive lung disease, inflammatory lung disease and chronic obstructive pulmonary disease. Asthma treatment is a particularly common use of MDIs.

MDIs may be used to deliver various types of active ingredients as appropriate to the medical condition of the patient being treated including, by way of example, bronchodilators ($\beta_2$ agonists and anticholinergics) and corticosteroids.

A metered-dose inhaler typically includes a canister made from aluminum or steel and an actuator. The canister houses a pharmaceutical (therapeutic) formulation, which generally includes one or more active ingredients and a liquefied gas propellant. The formulation may also include various other components, such as stabilizing excipients.

The canister includes the metering valve at one end. The metering valve is typically contained within a neck portion of the canister and includes a valve stem extending outwardly from the canister through which valve stem the pharmaceutical formulation is dispensed.

The canister may be positioned in an actuator, which may typically include an approximately cylindrical body portion into which the canister is received and a discharge nozzle or sleeve, often called a "valve stem block," which communicates with a discharge opening. The discharge opening may be a mouthpiece opening or nosepiece opening, as appropriate to the delivery mode and is configured accordingly. When the canister is fully received in the actuator body portion to achieve its operational configuration, a portion of the length of the valve stem of the metering valve is received in the actuator discharge sleeve. The actuator discharge sleeve typically includes a shoulder or ledge against which a forward-most end of the valve stem rests when the canister is fully received into the actuator body portion.

For actuation of the MDI to dispense the unit dose, the user presses the base of the canister to urge the canister forwardly into the actuator. The shoulder or ledge of the discharge sleeve prevents forward movement of the valve stem relative to the actuator. The valve stem is thus moved along a line of action relative to the container. In other words, the valve stem is depressed partially into the container. This depression of the valve stem results in the discharge of the unit dose of the pharmaceutical formulation through the valve stem and the stem block and consequently through the discharge opening for delivery to the patient. On release of the canister by the user, the valve stem is biased to return to its initial position.

A metered-dose inhaler contains enough of the pharmaceutical formulation in the canister for a certain number of actuations, equating to a certain number of unit doses. The number of doses is determined by the supplier of the MDI to ensure that for each actuation of the MDI within that number of doses, the patient consistently receives the same unit dose of the pharmaceutical active. However, the inhaler may continue to operate after the determined number of actuations has been reached. This carries the significant risk that for such "excess" actuations, the amount of pharmaceutical active being delivered to the patient may not be correct and in particular may be insufficient. It may be very difficult for a patient accurately to count the number of actuations (and thus the number of doses) used or delivered in order to ensure that the determined number of doses is not exceeded.

Although efforts have been made to provide mechanical dose counters, these dose counters may add significant cost and materials to the device and may be inaccurate. Mechanical dose counters may not be able to differentiate events when a dose is actually delivered as compared with other events, such as when a metered-dose inhaler is dropped on the ground or otherwise experiences movement that does not press the metering valve sufficiently for a dose to be delivered. Hence mechanical dose counters have not gained widespread acceptance from healthcare providers.

Electro-mechanical and electronic dose counters have also been proposed but have yet to achieve a sufficiently low cost and sufficiently high reliability. In particular, the problem of false counts (such us when the MDI is accidentally dropped) has not been resolved and difficulties persist and providing a power source which is suitably compact and cheap and which can reliably provide power throughout the full service life of the MDI.

US 2010/0078447 to Sauzade et el proposes a detection arrangement for detecting the dispensing of a fluid from a metering valve, such as of an inhaler for nasal use. The detector detects the passage of the fluid between the metering valve and a dispensing orifice and provides a "signal" intended to inform the user that a dose had been dispensed. In embodiments, the detector comprises a piezoelectric material, such as PVDF, in the form of a membrane which surrounds the channel through which the fluid is dispensed.

Pressure changes in the channel as fluid is dispensed cause a deformation of the membrane thereby generating the dispensing signal.

US 2011/0041845 to Solomon describes an MDI with a dose counter which relies on a force sensor located on the base of the canister. Actuation of the MDI by depression of the canister thus generates a force signal which is used to advance the dose counter. The requirement to place the force sensor on the base of the canister is disadvantageous, not least in terms of patient acceptance and compliance. The force sensor of US 2001/0041845 is also used to capture data relating to the pressure gradient and duration of each activation. An algorithm is used which advances the dose counter only when the detected pressure profile of the activation closely matches a previously determined profile known to be required in order to "fire" the canister and deliver a dose.

SUMMARY OF EMBODIMENTS OF THE INVENTION

In some embodiments, a dose counter for a metered dose inhaler having an activation valve at a valve end of the metered dose inhaler is provided. The dose counter includes a housing having a first end and an opposing second end, the housing first end configured to receive a metered dose inhaler valve end, and the second end defining a cavity. An actuation detection assembly is in the cavity of the housing. The actuation detection assembly includes an actuation detection element on the second end of the housing, and an activator element in the cavity of the housing. The activator element is configured to move between a first position in the cavity in which the activator element is spaced apart from the actuation detection element on the housing by a gap and a second position in which the activator element cooperates with the actuation detection element so that the actuation detection element generates an actuation signal.

In some embodiments, the activator element includes a biasing element having one or more biasing members that are configured to bias the activator element in the first position that is spaced apart from the actuation detection element.

In some embodiments, the housing includes a wall defining an aperture that is configured to receive an external cooperating element that cooperates with the activator element to move the activator element between the first and second position.

In some embodiments, the housing is configured to be positioned together with a metered dose inhaler canister in an actuator body such that when the metered dose inhaler canister is pressed toward a base of the actuator body, a portion of the actuator body is moved toward the activator element and moves the activator element from the first position to the second position. The portion of the actuator body that moves the activator element from the first position to the second position may include a sleeve configured to receive the activation valve of the metered dose canister.

In some embodiments, the dose counter includes a counter circuit positioned in the cavity. The counter circuit is configured to receive an actuation signal from the actuation detection element and to index a counter value responsive to the actuation signal. In some embodiments, the counter circuit is configured to determine whether the actuation signal satisfies one or more dose delivery parameters and to index the counter value if the one or more dose delivery parameters are satisfied. The actuation signal may include a force profile curve and the dose delivery parameters comprise an area of the force profile curve that is above a threshold value. An electrophoretic display may be mounted on the housing, wherein the counter value is displayed on the electrophoretic display.

In some embodiments, the counter circuit comprises a power supply, and the dose counter further comprising a projection in the housing that is configured to move between a first position in which the projection opens the counter circuit and a second position in which the projection allows the circuit to be closed so as to permit current flow from the power supply to activate the counter circuit.

In some embodiments, the housing is configured to be positioned together with a metered dose inhaler in an actuator body. The metered dose inhaler has an actuation valve for delivering a metered dose from the metered dose inhaler when the metered dose inhaler is pressed toward a base of the actuator body, and the actuator body includes the circuit activation pin thereon such that, when the metered dose inhaler is pressed toward the base of the actuator body, the circuit activation pin passes through the aperture of the housing and moves the projection from the first position to the second position. In some embodiments, the counter circuit comprises a circuit board having a power supply contact thereon, and the projection is positioned between the circuit board and the power supply in the first position such that the projection moves the power supply away from the power supply contact to thereby open the circuit. In some embodiments, the counter circuit further includes a biasing unit that is configured to bias the power supply in a direction toward the power supply contact such that when the projection moves to the second position, the power supply moves in the direction toward the power supply contact and the power supply closes the circuit to permit current flow.

In some embodiments, the biasing element includes a generally planar base, and the one or more biasing members extend away from the base and are configured to abut a portion of the housing to thereby bias the biasing element in the first position. The biasing element may include an actuation detection element activation plate configured to contact the actuation detection element in the second position. In some embodiments, the biasing members extend at an obtuse angle away from the base. In some embodiments, the biasing element rests directly or indirectly on, but is not fixedly attached to, other portions of the dose counter.

In some embodiments, the actuation detection element is mounted on a non-planar portion of the housing that is configured to increase a deflection of the actuation detection element in the second position.

In some embodiments, the actuation detection element comprises a PVDF film.

In some embodiments, the housing first end comprises one or more brackets configured for mounting the housing on a metered dose inhaler canister valve end.

In some embodiments, a metered-dose inhaler assembly includes a canister having a base end and a valve end opposite to the base end. The canister includes an activation valve on the valve end thereof. An actuator body has a canister receiving end and a dose dispensing end. The canister receiving end has an opening for receiving the canister therein and the dose dispensing end has an opening for dispensing a therapeutic agent from the canister. A dose counter includes a housing having a first end and an opposing second end. The housing first end is configured to receive the canister at the valve end thereof, and the second end defines a cavity. An actuation detection element is on the second end of the housing. An activator element is in the cavity of the housing, and the activator element is configured to move between a first position in the cavity in which the activator element is spaced apart from the actuation detection element on the housing by a gap and a second position in which the activator element cooperates with the actuation detection element so that the actuation detection element generates an actuation signal. The actuator body includes a cooperating element configured such that when the canister is moved relative to the actuator body from a rest position to a dispensing position, and the cooperating element moves the activator element from the first position to the second position.

In some embodiments, the activator element includes a biasing element having one or more biasing members that are configured to bias the activator element in the first position that is spaced apart from the actuation detection element.

In some embodiments, the housing comprises a wall defining an aperture that is configured to receive the cooperating element that cooperates with the activator element to move the activator element between the first and second position.

In some embodiments, the counter housing is configured to be positioned together with the metered dose inhaler canister in the actuator body such that when the metered dose inhaler canister is pressed toward the dose dispensing end of the actuator body, the cooperating element of the actuator body is moved toward the activator element and moves the activator element from the first position to the second position.

In some embodiments, the cooperating element of the actuator body that moves the activator element from the first position to the second position comprises a sleeve configured to receive the activation valve of the metered dose canister.

In some embodiments, the dose counter further includes a counter circuit positioned in the cavity of the counter, and the counter circuit is configured to receive an actuation signal from the actuation detection element and to index a counter value responsive to the actuation signal.

In some embodiments, the counter circuit is configured to determine whether the actuation signal satisfies one or more dose delivery parameters and to index the counter value if the one or more dose delivery parameters are satisfied.

In some embodiments, the actuation signal includes a force profile curve and the dose delivery parameters comprise an area of the force profile curve that is above a threshold value.

In some embodiments, an electrophoretic display is mounted on the housing, and the counter value is displayed on the electrophoretic display.

In some embodiments, the biasing element includes a generally planar base, and the one or more biasing members extend away from the base and are configured to abut a portion of the housing to thereby bias the biasing element in the first position.

In some embodiments, the biasing element comprises an actuation detection element activation plate configured to contact the actuation detection element in the second position.

In some embodiments, the actuation detection element is mounted on a non-planar portion of the housing that is configured to increase a deflection of the actuation detection element in the second position.

In some embodiments, the actuation detection element includes a PVDF film.

In some embodiments, the housing first end includes one or more brackets configured for mounting the housing on a metered dose inhaler canister valve end.

In some embodiments, a dose counter for a metered dose inhaler includes a housing configured to receive a metered dose inhaler canister. A circuit is positioned in the housing and having a power supply, and the circuit is configured to receive an actuation signal from an actuation detection element and to index a counter responsive to the actuation signal. A projection in the housing that is configured to move between a first position in which the projection opens the circuit and a second position in which the projection allows the circuit to be closed so as to permit current flow from the power supply to activate the circuit.

In some embodiments, the housing includes an aperture configured to receive a circuit activation pin that moves the projection from the first position to the second position.

In some embodiments, the housing is configured to be positioned together with a metered dose inhaler canister in an actuator body, and the metered dose inhaler has an actuation valve for delivering a metered dose from the canister when the metered dose inhaler is pressed toward a base of the actuator body. The actuator body includes the circuit activation pin thereon such that, when the metered dose inhaler canister is pressed toward the base of the actuator body, the circuit activation pin passes through the aperture of the housing and moves the projection from the first position to the second position.

In some embodiments, the circuit includes a circuit board having a power supply contact therein, and the projection is positioned between the circuit board and the power supply in the first position such that the projection moves the power supply away from the power supply contact to thereby open the circuit.

In some embodiments, a biasing unit is configured to bias the power supply in a direction toward the power supply contact such that when the projection moves to the second position, the power supply moves in the direction toward the power supply contact such that the power supply closes the circuit and permits current flow.

In some embodiments, the housing has a first end and an opposing second end. The housing first end is configured to receive a metered dose inhaler canister, and the second end defines a cavity, and the actuation detection element is mounted on the second end of the housing. The counter further includes an activator element in the cavity of the housing, and the activator element is configured to move between a first position in which the activator element is spaced apart from the actuation detection element on the housing by a gap and a second position in which the activator element cooperates with the actuation detection element so that the actuation detection element generates an actuation signal.

In some embodiments, the counter includes an electrical connection configured to transmit the actuation signal from the actuation detection element to the circuit.

In some embodiments, the activator element includes a biasing element having one or more biasing members that are configured to bias the activator element in the first position that is spaced apart from the actuation detection element.

In some embodiments, the housing includes a wall defining an aperture that is configured to receive an external cooperating element that cooperates with the activator element to move the activator element between the first and second position.

In some embodiments, the counter includes an electrophoretic display mounted on the housing that is configured to display a count value of the counter.

In some embodiments, a metered-dose inhaler assembly includes a canister having a base end and a valve end opposite to the base end. The canister includes an activation valve on the valve end thereof. An actuator body has a canister receiving end and a dose dispensing end, and the canister receiving end has an opening for receiving the canister therein and the dose dispensing end has an opening for dispensing a therapeutic agent from the canister. A dose counter includes a housing configured to receive the canister, a circuit positioned in the housing and having a power supply. The circuit is configured to receive an actuation signal from an actuation detection element and to index a counter responsive to the actuation signal. A projection is in the housing that is configured to move between a first position in which the projection opens the circuit and a second position in which the projection allows the circuit to be closed so as to permit current flow from the power supply to activate the circuit. The actuator body includes a cooperating element configured such that when the canister is moved relative to the actuator body from a rest position to a dispensing position, the cooperating element moves the projection from the first position to the second position.

In some embodiments, the counter housing includes an aperture configured to receive the cooperating element that moves the projection from the first position to the second position.

In some embodiments, the metered dose inhaler has an actuation valve for delivering a metered dose from the canister when the metered dose inhaler is pressed toward a base of the actuator body, and when the metered dose inhaler canister is pressed toward the base of the actuator body, the cooperating element passes through the aperture of the housing and moves the projection from the first position to the second position.

In some embodiments, the circuit includes a circuit board having a power supply contact therein, and the projection is positioned between the circuit board and the power supply in the first position such that the projection moves the power supply away from the power supply contact to thereby open the circuit.

In some embodiments, a biasing unit is configured to bias the power supply in a direction toward the power supply contact such that when the projection moves to the second position, the power supply moves in the direction toward the power supply contact such that the power supply closes the circuit and permits current flow.

In some embodiments, an electrophoretic display is mounted on the housing that is configured to display a count value of the counter.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 9 illustrates the circuit activation pin in an at rest position prior to circuit activation. FIG. 10 illustrates the circuit activation pin as it moves the battery tab out of the circuit. FIG. 11 illustrates the circuit activation pin in an at rest position after the battery tab has been moved out of the circuit and the battery rests on a battery contact.

DETAILED DESCRIPTION OF EMBODIMENTS OF THE INVENTION

Figure 1:
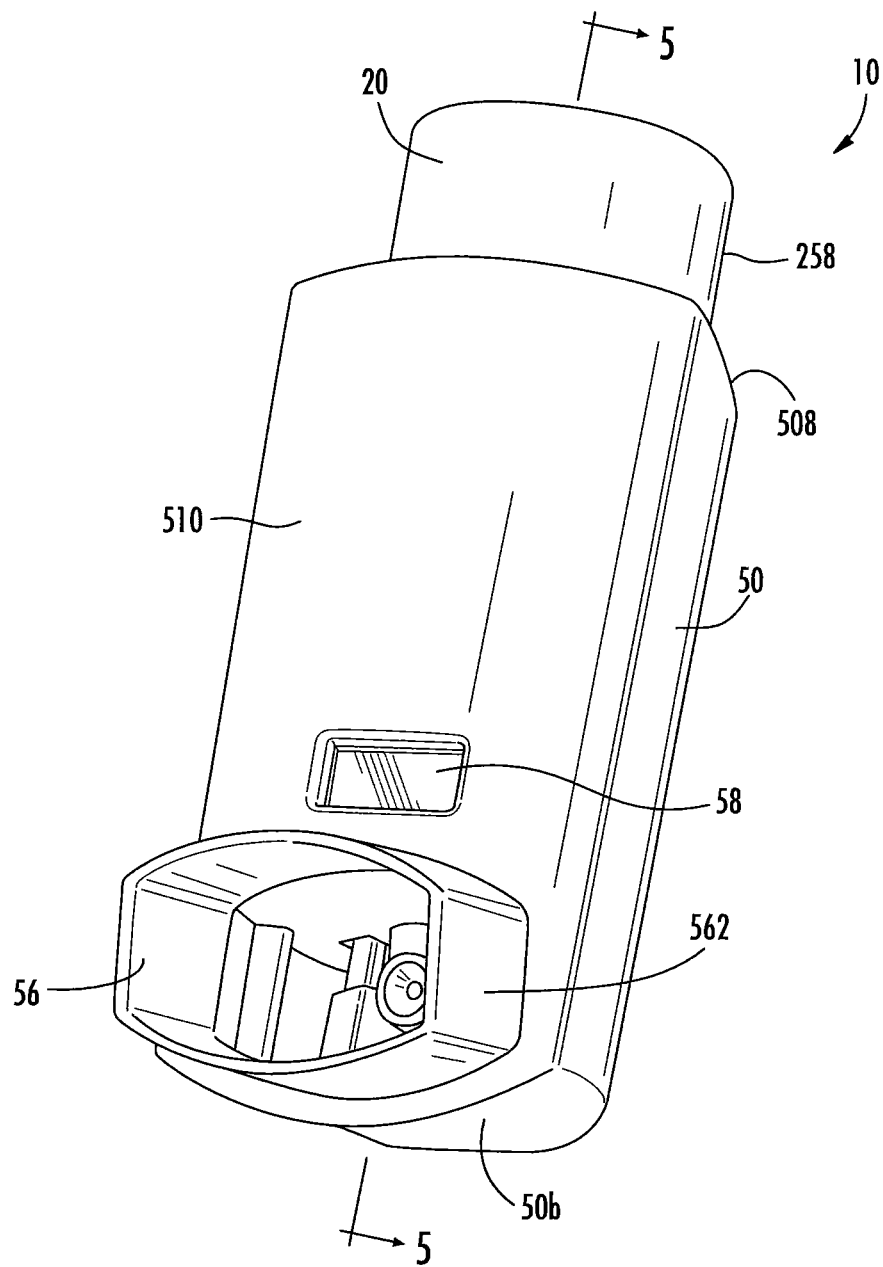
FIG. 1 is a perspective front view of a metered dose inhaler assembly according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "index" or "indexed", or grammatical or linguistic equivalents thereof, as used herein in connection with the dose counter refers either to an increment or a decrement of the dose counter, as appropriate to the context. Typically, the dose counter indexing will be a decrement, so that for each actuation of the MDI the counter is decremented by one and so that the dose counter display shows a remaining number of doses. It is, however, possible that dose counter indexing will be an increment, so that for each actuation of the MDI the counter is incremented by one and so that the dose counter display shows a number of doses which have been dispensed. For example, "indexing a counter value" includes either increasing or decreasing the counter value.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, circuit, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be a non-transient computer-readable medium, for example but not limited to, an electronic, electromagnetic, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

Figure 2:
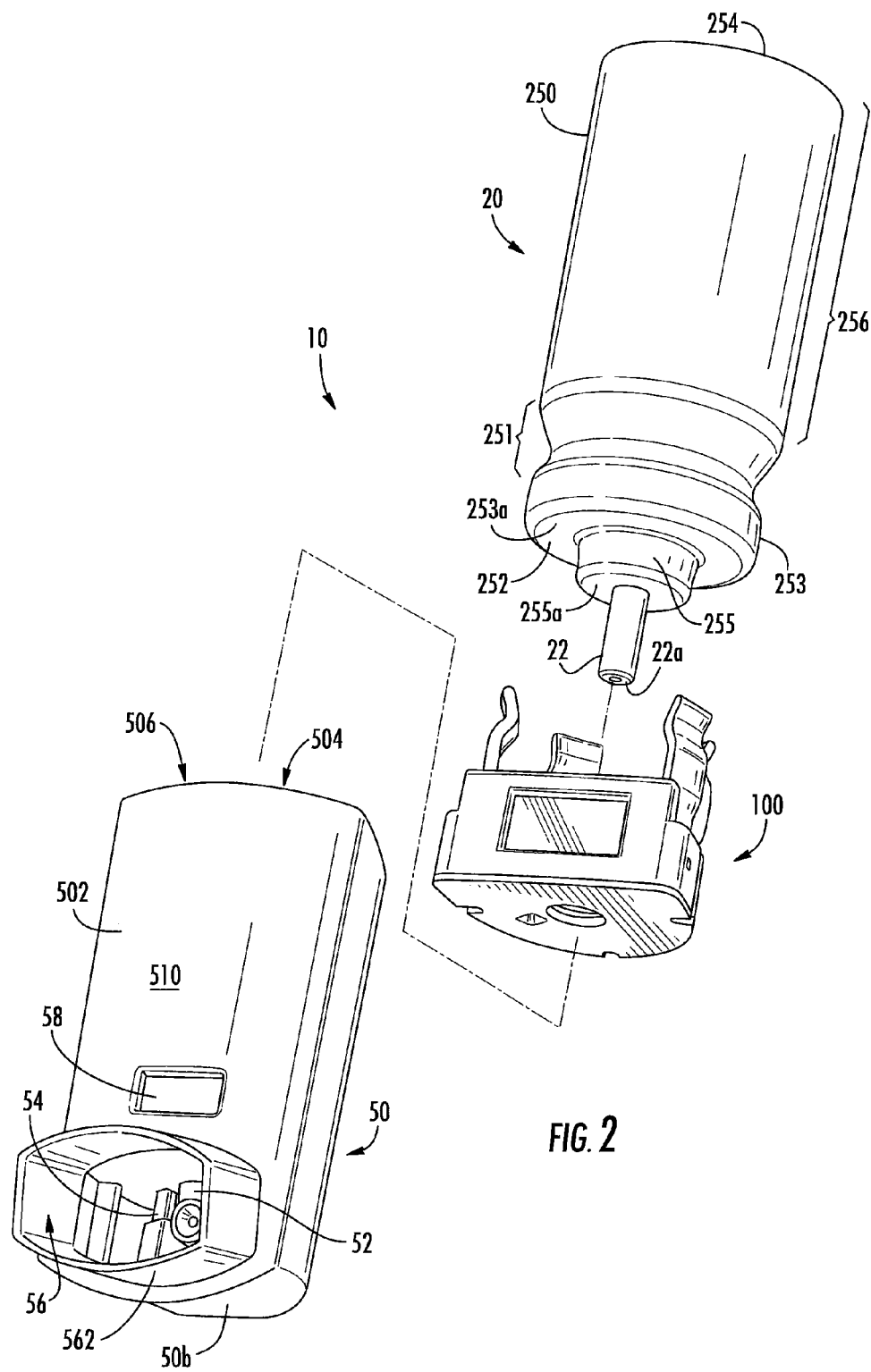
FIG. 2 is an exploded perspective view of the metered dose inhaler assembly of FIG. 1 illustrating the actuator, canister, and counter according to some embodiments.

Embodiments according to the present invention will now be described with reference to FIGS. 1-11. As shown in FIGS. 1-2, a metered-dose inhaler (MDI) assembly 10 includes a canister 20 in which the pharmaceutical formulation is contained, an actuator 50 and a counter 100 (FIG. 2).

A typical canister 20 includes a can or vial 250 and a metering valve having a valve stem 22. The can 250 is normally made of a metal such aluminum or steel and has a base 254, a main body portion 256 and a necked portion 251. The necked portion 251 defines a generally annular concavity formed at an end portion of the can 250. As manufactured, the can 250 has an open end adjacent the necked portion 251. The open end of the can 250 is closed by a metering valve housing 252. The metering valve housing 252 comprises a ferrule 253 which is crimped to a rim of the can 250 at the open end adjacent the necked portion 251, thereby to close the can 250. Typically the metering valve is contained, at least in part, in an upper valve housing portion 255 that includes a leading edge 255a. The upper valve housing portion 255 of a typical canister 20 is generally cylindrical and extends outwardly of the ferrule 253 away from the can base 254. The ferrule 253 includes a leading edge 253a. The working parts of the metering valve are thus positioned inside can 250, typically near the necked portion 251. Metering valves as such are well known in the art and the person skilled in the art of MDIs is familiar with their construction and operation. The metering valve includes a valve stem 22 extending outwardly of the canister 20, via the metering valve housing portion 255, through which a metered amount of a pharmaceutical formulation is dispensed. The valve stem 22 has a distal end surface 22a.

The actuator 50 includes a main body portion 502 which defines an interior chamber 504 into which the canister 20 is received through an open end 506. The chamber 504 is sized such that the valve stem 22, the metered valve housing 252, and the majority of the main body portion 256 of the canister 20 are received into the chamber 504. An upper (with respect to the orientation of the MDI assembly 10 as shown in FIG. 1) end portion 258 of the main body portion 256 of the canister 20 extends outwardly of the actuator 50, beyond an upper edge 508 thereof.

The actuator 50 further includes a discharge opening 56, which as illustrated, is shaped to be received into the user's mouth with the lips sealed against an outer surface 562. It should be understood that an MDI adapted for nasal delivery will have a differently shaped discharge opening, configured to fit into the nostril, as would be understood by one skilled in the art and is within the scope of the invention.

A display opening 58 is provided in a wall 510 of the actuator 50 in any suitable location such that the display of the counter 100 can be seen and read by the user.

Figure 6:
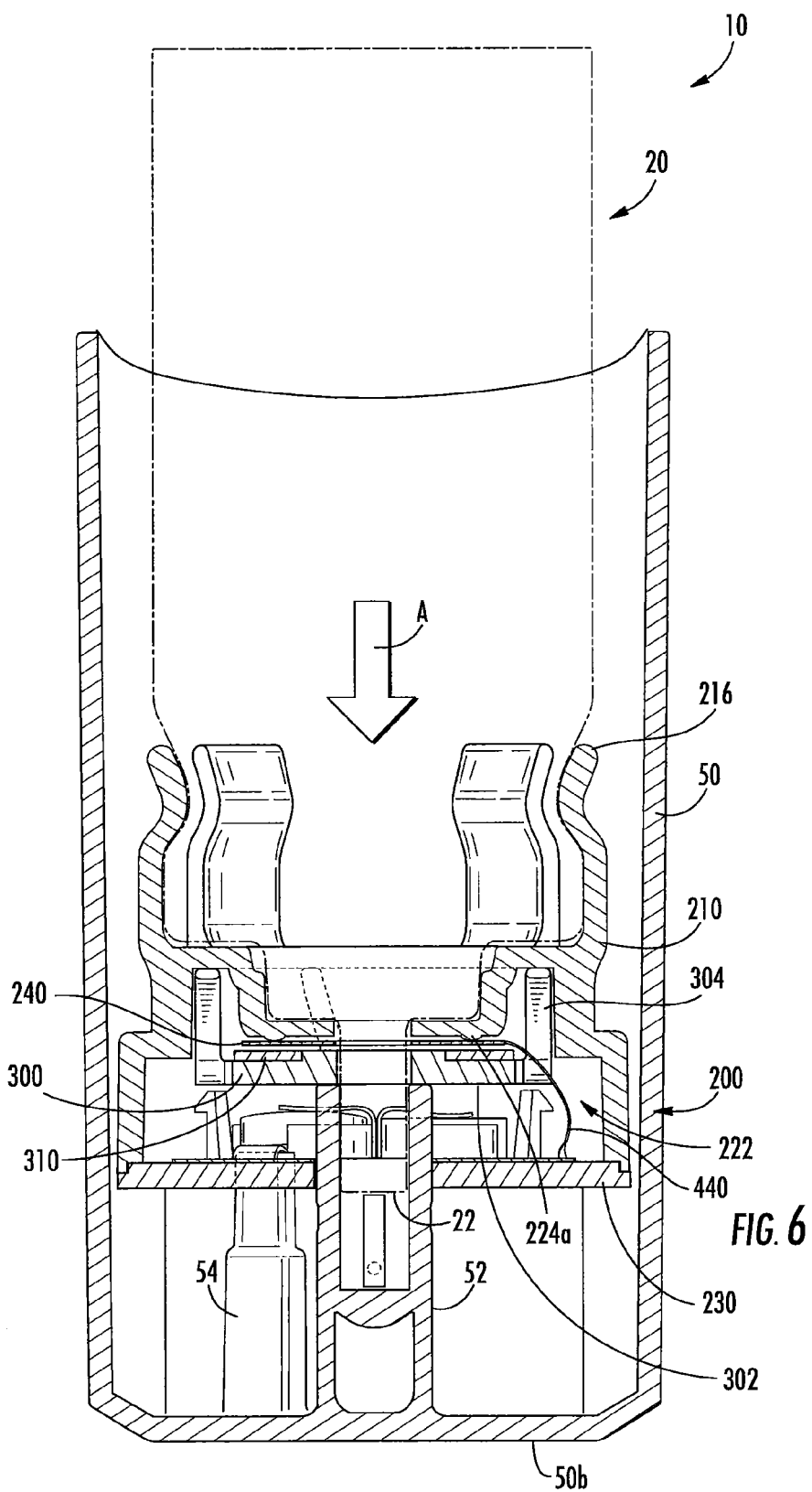

For actuation of the MDI assembly 10 (that is, to dispense a metered dose of the pharmaceutical formulation), the user applies force to the base 254 of the canister 20 to urge the canister to move in the direction shown by arrow A in FIG. 6. Typically the user depresses the base 254 of the canister 20 with a finger or thumb. Thus the canister 20 moves further into main body portion 502 of actuator 50 towards a lower end wall 50b of the actuator 50.

The actuator 50 includes an interior sleeve or stem block 52 which cooperates with the valve stem 22 when the canister 20 is pressed into the actuator 50 to limit or prevent movement of the valve stem 22 in the direction of arrow A (i.e., forward movement of the valve stem 22 toward the lower end wall 50b). The sleeve 52 may include a shoulder, ledge or other constriction element which cooperates with a forward part of the valve stem 22, such as the end surface 22a, for preventing such forward movement. Thus, on actuation of the MDI assembly 10, the valve stem 22 moves relative to the canister 20 in the direction opposite to the direction of arrow A. This depression of the valve stem 22 moves the metering valve into its dispensing condition and a dose of the pharmaceutical formulation is dispensed through the valve stem 22.

The interior sleeve 52 defines a fluid flow path from the chamber 504 to discharge opening 56. Since the valve stem 22 is received in the sleeve 52 of the actuator 50, on actuation of the MDI assembly 10, the pharmaceutical formulation is dispensed via the valve stem 22 and the fluid flow path to the discharge opening 56.

Figure 3:
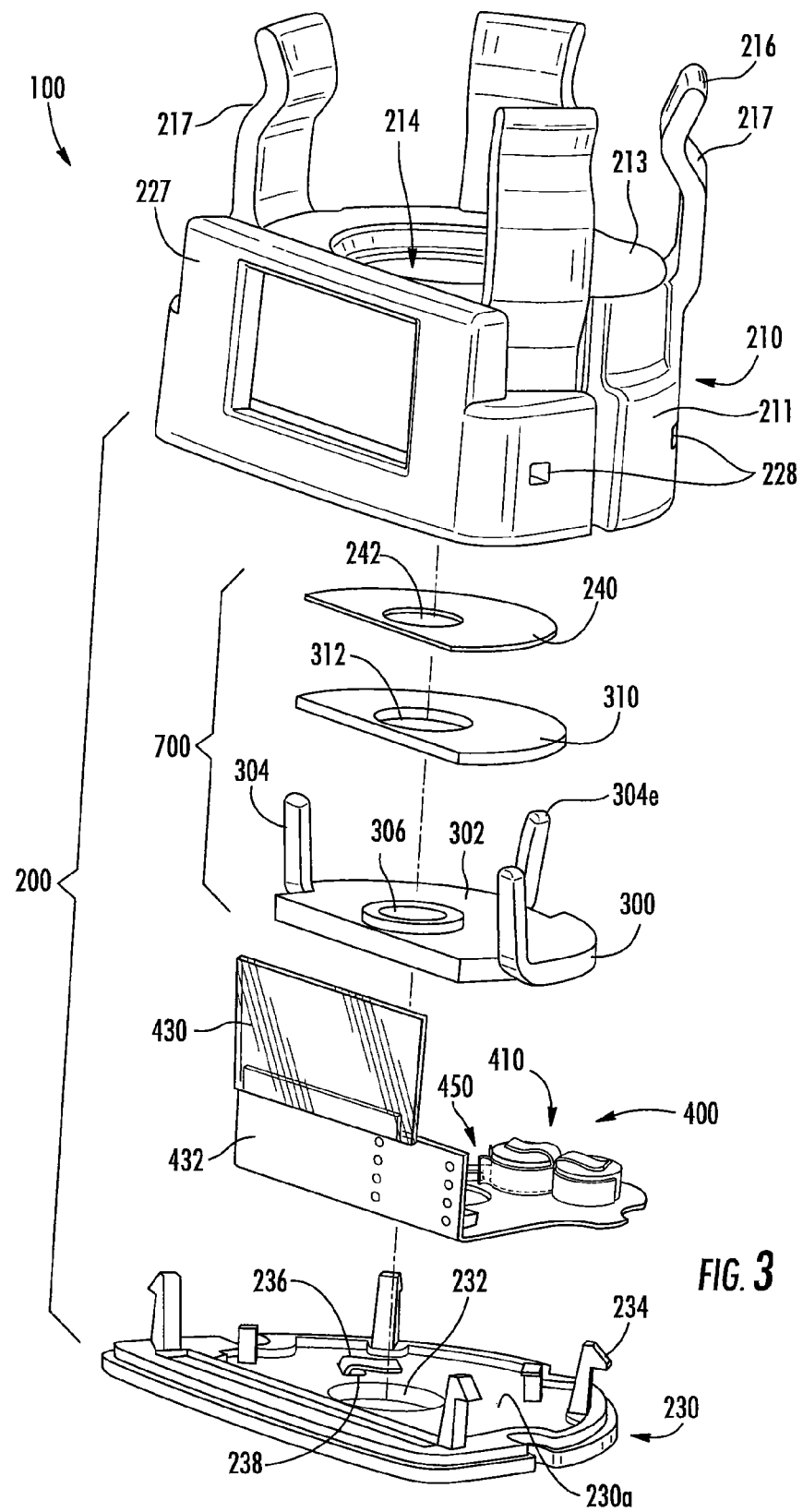
FIG. 3 is an exploded top perspective view of the counter of FIG. 2 according to some embodiments.
Figure 4:
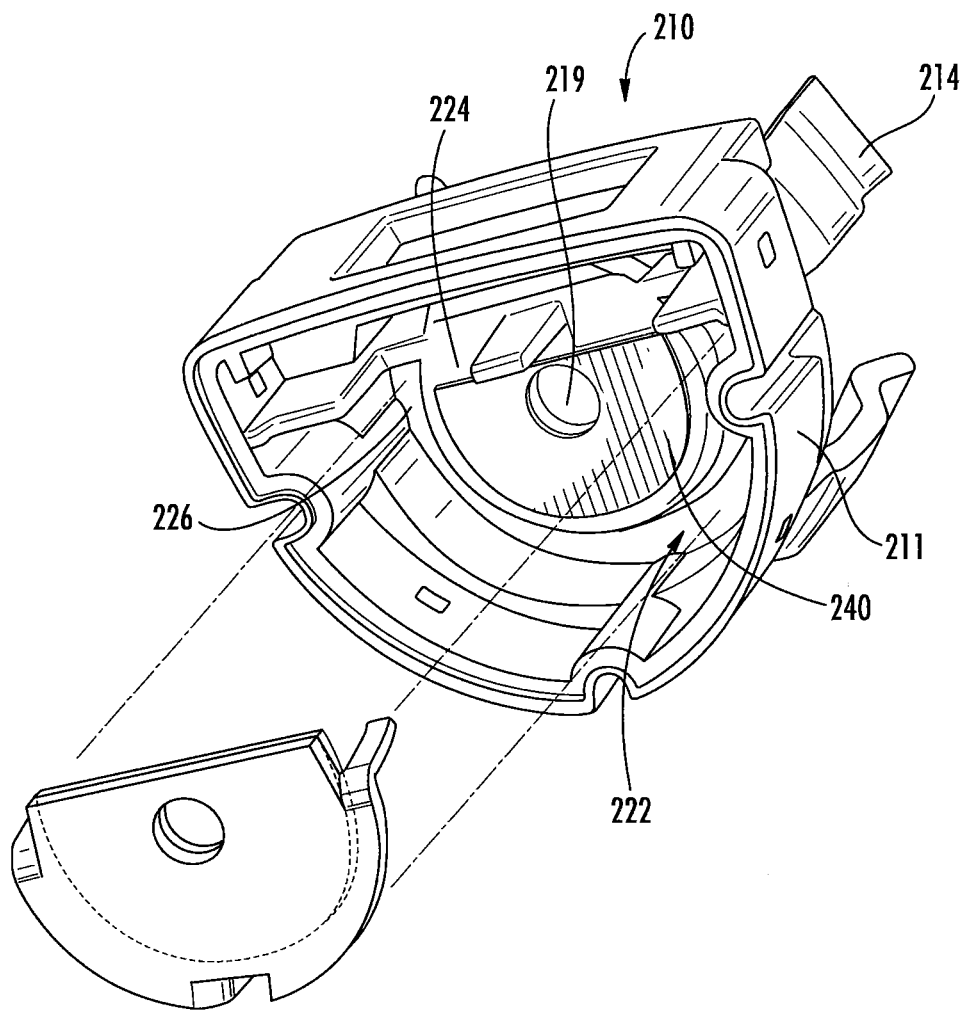
FIG. 4 is an exploded bottom perspective view of a portion of a housing, force sensor and spring unit of the counter of FIG. 2.

As illustrated in FIGS. 3-4, the counter 100 includes a housing 200 having an upper housing portion 210 and a lower housing portion 230. An actuation detection assembly 700 includes a biasing element 300. An actuation detection element 240 is positioned inside the housing 200 together with an electrical assembly 400.

The housing portion 210 includes a side wall 211 depending from a top housing wall 213. The top housing wall 213 includes a substantially planar annular region which defines a centrally located aperture 214. Resiliently deformable legs or prongs 216 extend upwardly at the margin of the top housing wall 213 and are configured to receive the canister 20. In the illustrated example, the legs 216 include indented regions 217 which are shaped to conform with, and be located in, the necked portion 251 of the canister 20. In this way, the housing 200 is securely, and in some embodiments, removeably, mounted on the canister 20. This configuration of mounting the housing 200 on the canister 20 may be convenient and simple; however, it should be understood that other configurations may be used, for example, where differently shaped canisters 20 are used in the MDI assembly 10. In particular embodiments, the canister 20 is securely and removeably attached to the housing 200. It should be understood, however, that the canister 20 may be more permanently affixed to the housing 200 without departing from the scope of the invention.

The side wall 211 of the housing portion 210 further includes a display frame portion 227 and apertures 228. As illustrated, the display frame portion 227 is generally planar. In some configurations, the side wall 211 may be sized and configured such that the assembled housing 200 and canister 20 will fit into the chamber 504 of the actuator 50 in only one orientation. In such a configuration, the display frame portion 227 may be located in alignment with the aperture 58 of the actuator 50.

The upper housing portion 210 further includes an internal housing wall 215 arranged below (with respect to the orientation of the MDI assembly 10 shown in FIG. 5) and generally parallel to the top housing wall 213. The internal housing wall 215 is annular and defines an inner central aperture 219. The internal housing wall 215 is linked to the top housing wall 213 by a generally cylindrical inner wall 221 which extends from the margin of the top housing wall 213 and defines aperture 214 so that the internal housing wall 215 and inner wall 221 together define a generally cylindrical well 223.

The housing portion 210 defines an interior cavity 222 therein (FIG. 4) bounded by the side wall 211, the internal housing wall 215, the cylindrical inner wall 221 and the top housing wall 213. The cavity 222 includes a generally planar region 224, which includes at least a portion of the underside of the internal housing wall 215, and a planar recessed region 226, which includes an underside of the top housing wall 213. As illustrated in FIG. 5, the planar region 224 may include protrusion 224a or other surface variation.

As illustrated in FIGS. 3-4, the lower housing portion 230 includes a generally planar web portion 230a, which is at least approximately shaped to conform to the circumferential profile of the side wall 211, such that the lower housing portion 230 forms an at least partial closure of the interior cavity 222. The web portion 230a defines a valve aperture 232. The valve aperture 232 is sized and located to permit passage therethrough of the interior sleeve 52 of the actuator 50. A plurality of upstanding latching prongs 234 extend from the web portion 230a. The prongs 234 of the lower housing portion 230 form a snap-fit with the corresponding apertures 228 of the upper housing 210.

As illustrated in FIGS. 2-7, the canister 20 is held in position by the prongs 216 of the housing portion 210. The end portion of the canister 20 extends through the aperture 214 of the housing 200 such that the upper valve housing portion 255 is received in the well 223. As can be seen in particular from FIG. 5, the well 223 is configured such that, with the canister 20 fully inserted into the actuator 50 in a rest (non-actuating) position, the leading surface 255a of the upper valve housing portion 255 is juxtaposed and, in some embodiments, abuts with inner housing wall 215, and the leading surface 253a of the ferrule 253 is juxtaposed and, in some embodiments, abuts with the top housing wall 213. It follows that, on actuation of the MDI assembly 10, force applied by the user to the end 254 of the canister 20 causes movement of the canister 20 further into the actuator 50, and such motion is transferred directly to the housing 200 so that the housing 200 also moves further into the actuator 50, as indicated by arrow A in FIGS. 6 and 7.

Figure 5:
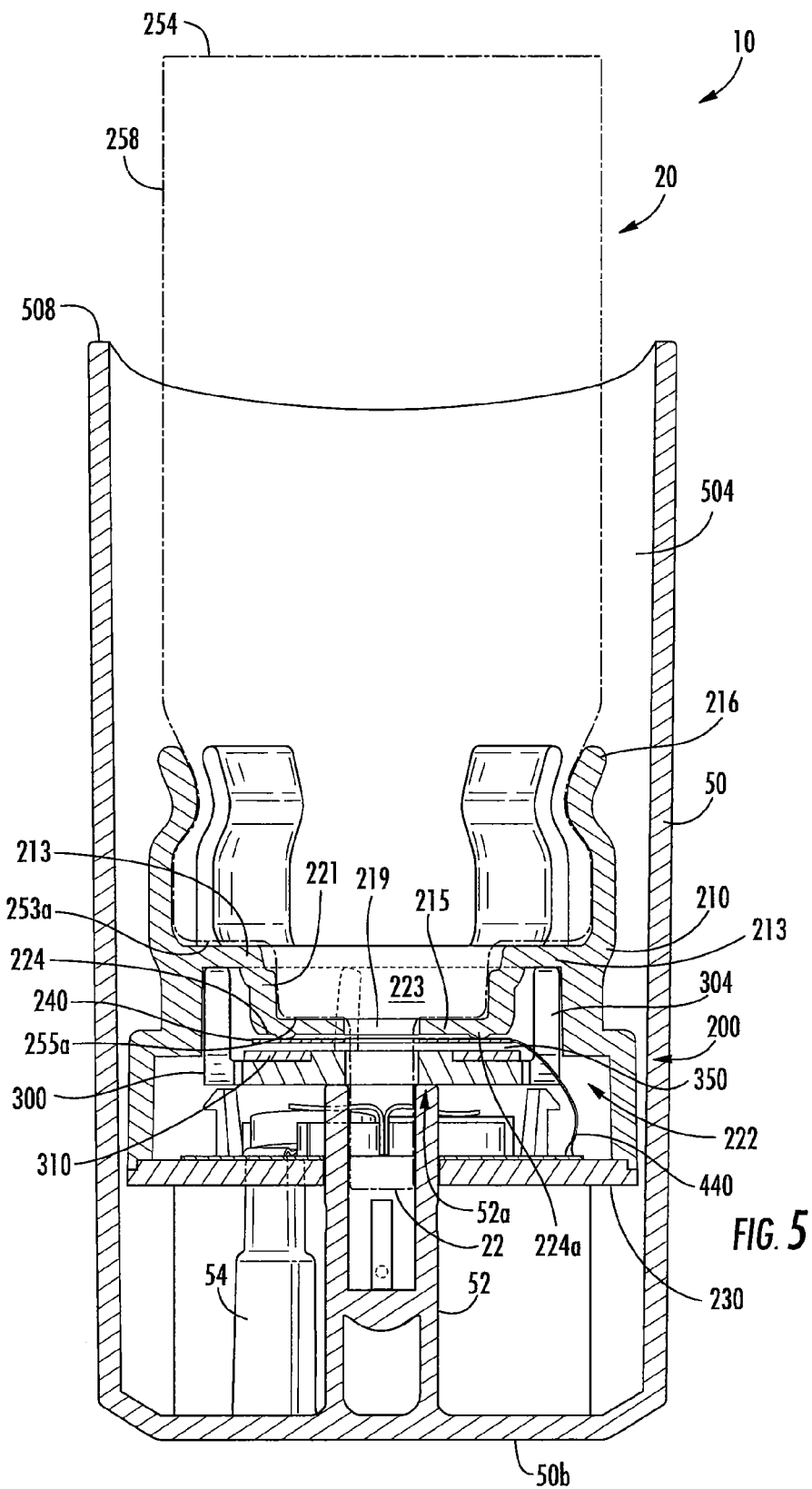
FIGS. 5-7 are cross sectional views of the metered dose inhaler assembly of FIG. 1. The canister and counter are shown in an at rest position (FIG. 5), the movement of the canister as it is depressed (FIG. 6), and a fully actuated position (FIG. 7) in which a dose is counted by the counter.
Figure 7:
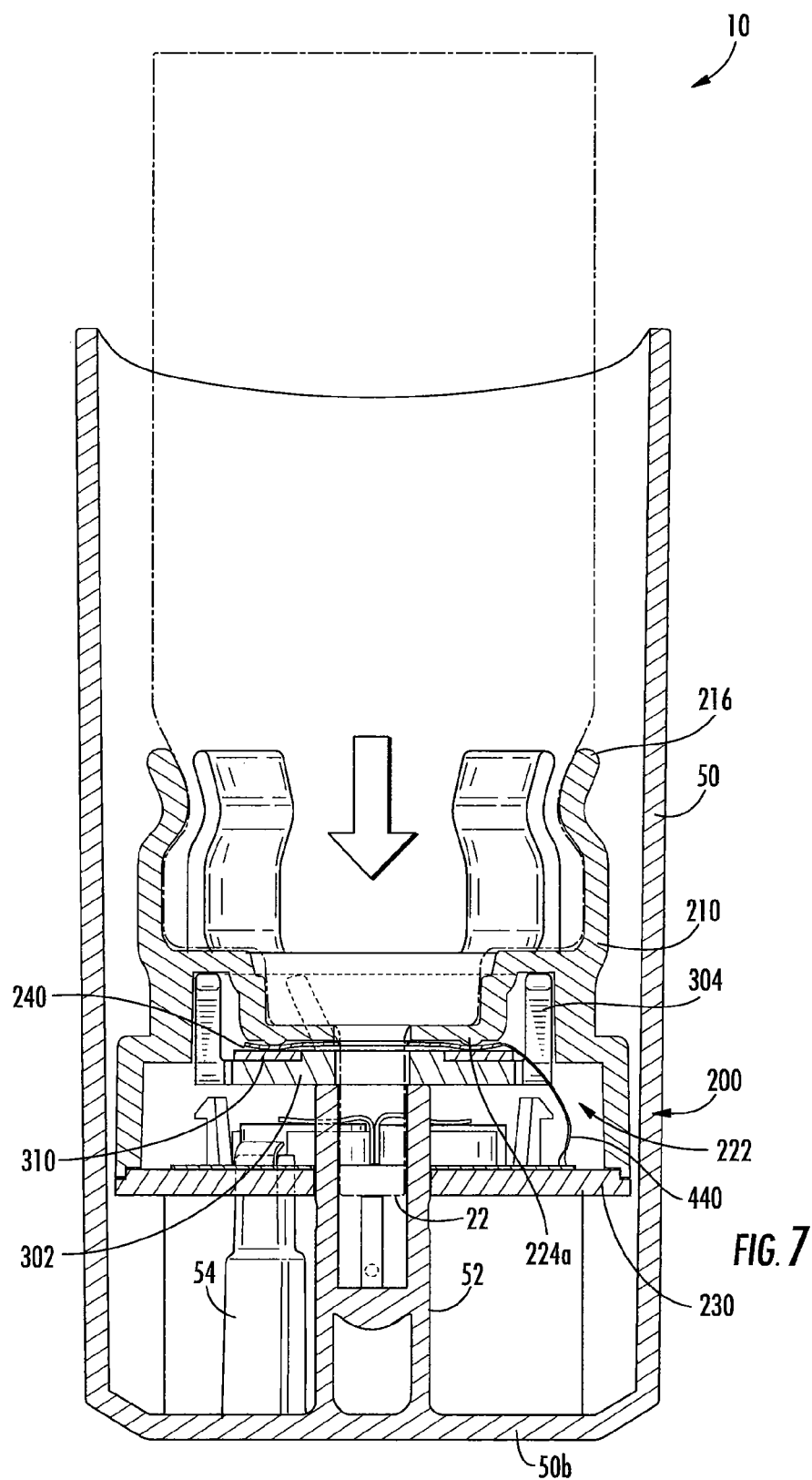

As can be seen in particular from FIGS. 5, 6 and 7, in the illustrated example, the top housing wall 213, inner housing wall 215 and the cylindrical inner wall 221 are sized and shaped to generally conform to the size and shape of the ferrule 253 and the upper valve housing portion 255 of the canister 20. It should be understood that any suitably cooperating configurations may be used. For example, if the canister 20 has a different shape from that illustrated in the Figures, the corresponding portions of the housing 200 can have different shapes, adapted or configured to work with the different canister shape, provided that motion imparted by the user to the canister 20 for actuation as discussed above is transferred to the housing 200.

The valve stem 22 extends through aperture 232 of the lower housing portion 230 and is received in the interior sleeve 52 of the actuator 50.

As noted above, the actuation detection assembly 700 comprises a biasing element 300 and an actuation detection element 240. The actuation detection assembly 700 may optionally further include an activation plate 310. The actuation detection element 240 is mounted on the planar portion 224 of the cavity 222. The actuation detection element 240 includes an aperture 242 for passage therethrough of the valve stem 22. The actuation detection element 240 is configured to provide an output to the electrical assembly 400 on actuation of the MDI assembly 10.

Figure 8:
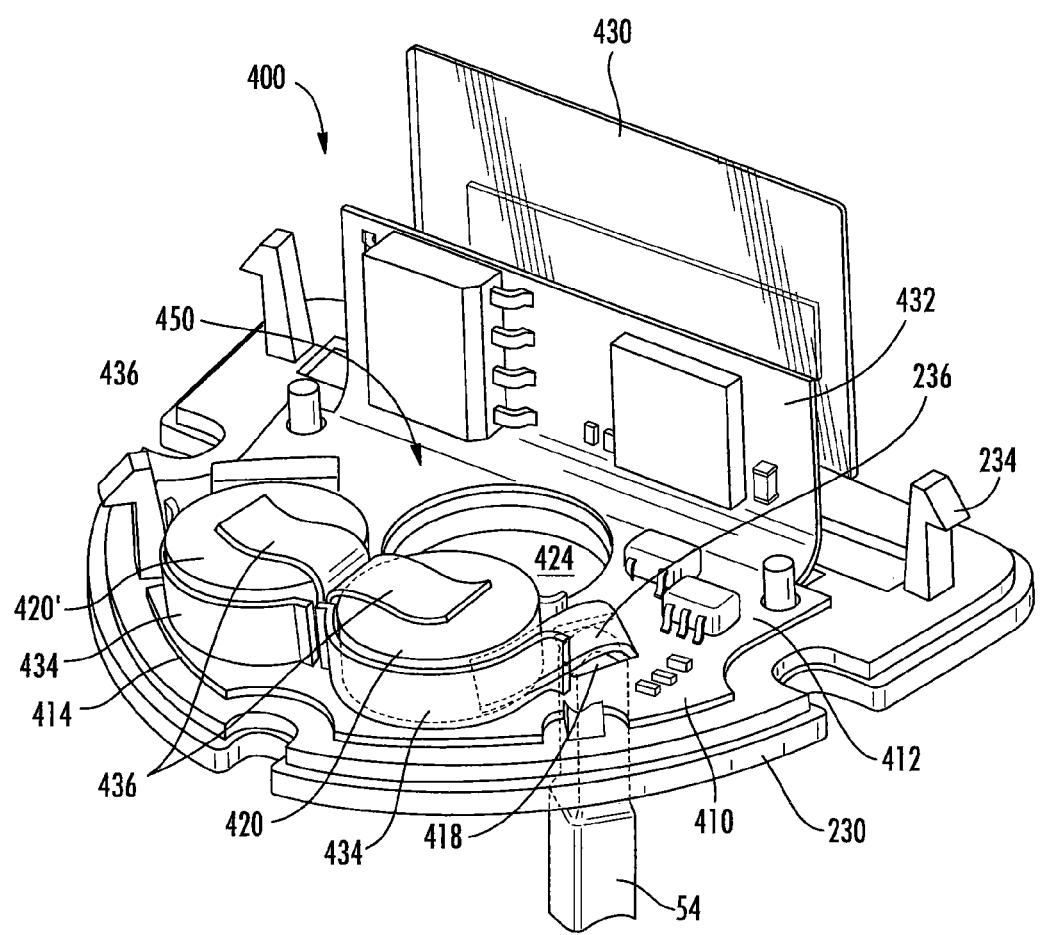
FIG. 8 is an enlarged top perspective view of a bottom housing portion and the electrical assembly of the counter of FIG. 2 together with a circuit activation pin of the actuator of FIG. 1 according to some embodiments.

The electrical assembly 400 is contained within the cavity 222. As shown in FIG. 8, the electrical assembly 400 includes a circuit board 410, a display 430, a display holding member 432 that is connected to the circuit board 410 and supports the display 430, a circuit substrate 412 that defines an exterior perimeter 414 and one or more power supplies, typically in the form of electrical cells or batteries 420, 420' which supply power to the a counting circuit 450. The electrical assembly 400 further includes a valve stem aperture 424 which is generally co-extensive with aperture 232 of lower housing portion 230.

The counting circuit 450 is configured to receive an input from the actuation detection element 240 and to index a counter value that is displayed on the display 430 and/or stored in a memory of the counting circuit 450 in response to the input. In some embodiments, the input from the actuation detection element 240 is subject to analysis by components of the electric assembly 400 to determine whether defined threshold conditions are met. If such conditions are not met, the counter value is not indexed.

As shown, for example, in FIG. 3, the biasing element 300 includes a generally planar portion 302, a plurality of biasing members 304, and an aperture 306. The biasing members 304 are, in some embodiments, in the form of upstanding legs and depend from, and extend generally upwardly from, the planar portion 302. The biasing members 304 are constructed to be resiliently deformable and typically are made from a suitable plastic.

Although embodiments according to the present invention are described herein with respect to the biasing element 300 with a plurality of biasing members 304, it should be understood that any suitable configuration may be used. For example, the biasing members 304 may be replaced with an alternative biasing component, such as a compression spring, and/or a different number (more or less) of biasing components could, in principle, be used. However, the biasing element 300 having the resiliently deformable biasing members 304 as illustrated may be provided with reduced cost, weight, ease of manufacture and assembly and functional effectiveness.

In some embodiments, the biasing element 300 is generally free-floating inside the housing 200 (although non-free-floating arrangements are possible, as discussed below). By "free-floating," it is meant that the biasing element 300 is not fixedly attached to any part of the housing 200.

In the illustrated embodiment, an actuation member, such as an activation plate 310 having an aperture 312, is mounted on the planar portion 302. The aperture 242 of the actuation detection element 240, and apertures 312 and 306 are aligned with the aperture 232 of the lower housing portion 230 to permit passage through each of the valve stem 22.

As shown in FIG. 5, in a rest position prior to actuation of the MDI assembly 10, the biasing members 304 of the biasing element 300 are in a non-deformed condition. The planar portion 302 of the biasing element 300 rests on an uppermost edge 52a of the sleeve 52 of the actuator so that the biasing element 300 is prevented by the sleeve 52 from any movement towards the bottom end of the actuator 50 (that is, in the direction of arrow A). Uppermost end parts 304e of the biasing members 304 contact the planar recessed region 226. The non-deformed length of the biasing members 304 (i.e. the dimension between end parts 304e and planar portion 302) is selected such that a gap 350 is maintained between the activation plate 310 of the biasing element 300 and the force sensor 240. That is, in the absence of significant force against the biasing element 300, the biasing members 304 are sized and positioned to maintain a separation or gap 350 between the plate 310 and the force sensor 240.

As shown in FIGS. 6-7, when, for actuation of the MDI assembly 10, a user exerts a downward pressure on the canister 20, the housing 200 moves together with the canister 20 toward the bottom end of the actuator 50, in the direction of arrow A. As noted above, the biasing element 300 cannot move with the housing 200 relative to the actuator 50 because the sleeve 52 of the actuator 50 is pressed against the base portion 302 of the biasing element 300. Accordingly, the biasing element 300 moves relative to the housing 200 with the result that the biasing members 304 are resiliently deformed (that is, they bend and flex). The activation plate 310 is thus pressed closer to the actuation detection element 240 (FIG. 6) until the activation plate 310 contacts the actuation detection element 240 and the gap 350 is eliminated (FIG. 7).

After actuation, the user releases the canister 20. The canister is returned to its rest position, typically under the action of a biasing means of the metering valve (such as a compression spring) acting on the valve stem 22. The biasing element 300 is also returned to its rest position as the biasing members 304 return to their un-deformed condition. The gap 350 between the activation plate 310 and the force sensor 240 is thus re-established, ready for the next actuation of the MDI assembly 10.

When the activation plate 310 contacts the actuation detection element 240, the actuation detection element 240 generates its output. Some forms of the actuation element 240 may include materials which generate a response when subject to compression, force and/or deformation. For example, piezoelectric materials and PVDF materials, which generate electrical charge in response to applied mechanical stress, i.e., compression and/or deformation, may be used. The magnitude of the charge generated by a piezoelectric material can be directly related to the extent and/or degree of compression or deformation of the piezoelectric material. The extent and/or degree of compression or deformation may be related to the force applied to the material. Hence, a relationship can be established between the force and/or mechanical deformation applied to the piezoelectric material and the charge which is generated as a result.

Thus, in some embodiments of the present invention, the actuation detection element 240 may include a piezoelectric material. On actuation of the MDI assembly 10, the biasing element 300 is urged against the actuation detection element 240, either directly or via the interposed activation plate 310. This results in sufficient compression and/or deformation of the actuation detection element 240 to generate a charge which is employed as an actuation signal. The generated actuation signal may be indicative of both the magnitude and duration of the force applied to the actuation detection element 240.

In some embodiments, for example, as shown in FIG. 3, the biasing element 300 rests directly or indirectly on, but is not fixedly attached to, other portions of the dose counter 100. Stated otherwise, the biasing element 300 is generally free-floating within the housing 200 and is sized and shaped so as to abut and fit generally snugly within the housing 200 without being connected or fixed with respect to either the housing 200 or elements within the housing 200. The biasing element 300, therefore, may move slightly in the longitudinal direction and/or lateral direction with respect to the dose counter 100 while still maintaining the gap between the activation plate 310 and the force sensor 240 in an inactive position until activated by the patient. In this configuration, the configuration of the counter 100 may eliminate or reduce the number of false counts. False counts refer to the instances when the canister 20 has not been depressed by a patient to deliver a dose, yet a count is incorrectly registered. Moreover, as illustrated, the biasing members 304 are formed at an obtuse angle that extends away from the base planar portion 302. Some conventional counters may require significant additional force to depress the canister within the actuator when the counter is in place and/or add additional height to the actuator and canister assembly. The additional force required to advance a counter and/or any increase in the size of the device due to the presence of the counter may create difficulties for patients, especially patients with arthritis or other physical conditions in which the actuator may be difficult to grasp. In contrast, in some embodiments, the obtuse angle of the biasing members 304 and the free-floating configuration of the biasing element 300 may reduce or eliminate any additional force needed by a user to depress the canister 20 so that the feel of the canister 20 to the patient during use is very similar with or without the counter 100 in the actuator 50. In addition, the counter 100 fits within the actuator 50 so that the spatial relationship of the canister 20 and the actuator 50 (e.g., the total height of the canister 20 and the actuator) are generally unchanged regardless of whether the counter 100 is being used. As illustrated in FIGS. 5-7, the actuation detection element 240 is electrically connected to the circuit board 410 by an electrical conduit or wire 440 so that the actuation signal from the actuation detection element 240 may be electrically communicated to the electrical assembly 400 via the wire 440. The counting circuit 450 receives the signal from the actuation detection element 240, analyzes the signal and counts an activation of the canister valve 22 and a delivery of a metered dose if the actuation signal from the sensor 240 indicates that a sufficient force has been applied to the actuation detection element 240 to indicate the delivery of a dose, the force applied to the actuation detection element 240 being directly related to the force applied by the user to the canister 20 for actuation. The analysis of "sufficient force" may include the duration of the force as well as the magnitude of the applied force.

Any suitable interface configuration may be used to contact the actuation detection element 240 such that the actuation detection element 240 generates an actuation signal e.g., as shown in FIG. 7. As illustrated, the region 224 has protrusions 224a thereon, which may result in increased deflection or curvature of the actuation detection element 240 when it comes into contact with the activation plate 310. Therefore, in some embodiments, the actuation detection element 240 may be positioned on a surface that is non-planar so as to increase a deformation of the actuation detection element 240 during an actuation of the counter 100. The protrusions 224a may be in any suitable position or configuration, including circular dimples or linear or curved regions, such as a groove that may extend circumferentially around a portion of the region 224. The non-planar interface resulting from the protrusions 224a and the deflection of the actuation detection element 240 in the actuated position of FIG. 7 may increase the sensitivity and/or magnitude of the actuation signal from the actuation detection element 240. Accordingly, the actuation detection element 240 may generate the actuation signal in response to the deflection and/or compression of the element 240. In some embodiments, however, the protrusions 224a may be omitted and the planar region 224 of the housing 210 and the activation plate 310 on the planar portion 302 of the biasing element 300 may provide a generally planar interface such that the actuation detection element 240 may generate an actuation signal in response to the compression thereof without necessarily requiring a deflection of the actuation detection element 224. In some embodiments, the interface between the planar region 224 (with or without the protrusions 224a), the actuation element 224, and the activation plate 310 and/or biasing element 300 may be selected to increase a sensitivity of the actuation signal and to reduce a likelihood of false readings from valve actuations that do not result in an actual dose delivery, for example, when the assembly 10 is accidentally dropped or otherwise moved in such a way that an actuation signal is generated by the actuation detection element 240.

The actuation detection element 240 may be in the form of a thin web or film of piezoelectric material, such as a PVDF (polyvinylidene fluoride, or polyvinylidene difluoride) film. The PVDF film may be supported on an appropriate substrate, the substrate being applied to the planar portion 224 of the cavity 222.

In some embodiments, the activation plate 310 may be a metal plate that increases the sensitivity with which the actuation detection element 240 generates an actuation signal and/or may be non-planar. For example, the actuation detection element 240 may be a PVDF film, which generally has increased sensitivity when activated by contact with a metal material.

Although embodiments according to the invention are described with respect to the actuation detection element 240 that is mounted on the planar region 224 of the housing 210 and an activation plate 310 on the planar portion 302 of the biasing element 300, it should be understood that other configurations may be used. For example, the activation plate 310 may be omitted, and the actuation detection element 240 may be contacted directly by the biasing element 300.

As illustrated, the biasing element 300 is generally free-floating inside the housing 200; however, the biasing element 300 or a portion thereof (such as the biasing members 304) may be mounted on a portion of the housing 200 or provided as an integral unit together with the housing 210.

Moreover, as illustrated, the biasing element 300 is configured to move between a position in which the activation plate 310 is separated from the actuation detection element 240 by a gap and an activated position in which the activation plate 310 is in contact with the actuation detection element 240 so that the actuation detection element 240 generates an actuation signal. However, it should be understood that any suitable activator element may be used to perform some or all of the functions of the biasing element 300. Stated otherwise, any activator element may be used that is configured to move, responsive to the activation of the valve 22 of the canister 20, between a position that does not generate a signal in the actuation detection element 240, such as a position having a gap 350 between the element and the actuation detection element 240, and a position in which the activation detection element 240 contacts the activator element to generate a signal at the activation detection element 240.

In some embodiments, the actuation detection element 240 may be provided as a conductive material or layer applied to the inside of the housing 200 that mates with a corresponding conductive material or layer (such as the activation plate 310 or other conductive material) applied to the biasing element 300. The conductive materials are configured to close a circuit when the biasing element 300 contacts the actuation detection element 240. Although the actuation detection element 240 is illustrated in FIGS. 5-7 as a deformable element, such as a PVDF layer, it should be understood that any suitable conductive material may be used. For example, a contact pad or a conductive thin film layer, such as a metal paint (e.g., carbon or nickel paint), a charged/polarized shim or metal plate, or multiple staged metal layers, may be applied to the inside of the housing 200 and to the biasing element 300 at the planar portion 302 thereof. In some embodiments, the housing 200 and, in particular, the actuation detection element 240, may be formed of an elastomeric material that is embedded with certain materials, such as carbon nanotubes, to provide conductive regions. Thus, the detection element 240 may be provided as a separate member or integrated together with the housing 200. During activation of the canister 20, the conductive layers of the inside of the housing 200 and the biasing element 300 contact one another. The electrical conduit or wire 440 is connected to a circuit, such as the counting circuit 450, on the circuit board 410. The counting circuit 450 includes a small power supply connected to the wire 440, which may be formed as a conductive loop that is configured to close a circuit when the conductive layers are in a closed or contacting position. However, in some embodiments, a degree of movement may be detected, such as with multiple staged layers, to determine whether a full actuation has been achieved.

Accordingly, when the conductive layers (illustrated as the activation plate 310 and the actuation detection element 240) on the housing 200 and on the biasing element 300 are in the open position shown in FIG. 5, then the counting circuit 450 is an open circuit. When the conductive layers on the housing 200 and on the biasing element 300 contact one another as shown in FIG. 7, the counting circuit 450 becomes a closed circuit, senses a signal and registers an activation of the canister 20. The wire 440 may be provided as a flexible printed circuit board or other conductive material that is suitable to carry a current. In addition, the conductive layers on the housing 200 and the biasing element 300 may be formed in any suitable shape and/or size such that the conductive layers are configured to contact and form an electrical connection to close the counting circuit 450 when the canister 20 is in the activated position shown in FIG. 7.

In some embodiments, the closure of the counting circuit 450 by the connection of the conductive layers is detected as a presence of a current and the opening of the counting circuit 450 is detected as an absence of a current. Accordingly, the conductive layers may be configured so that movement of the conductive layers by the housing 200 and the biasing element 300 during normal movement of the device 10 in which the canister 20 is not activated is not sufficient to close the circuit 450 by contacting the conducting layers and close the counting circuit 450. Moreover, complex analysis of a signal by the counting circuit 450 may be reduced or eliminated because the counting circuit 450 may be increased or indexed by one activation count when a voltage is detected, and analyzing a signal to determine if the force was sufficient to activate the canister may be unnecessary.

In some embodiments, the electrical assembly 400 is further provided with one or more components which act to keep open the counting circuit 450 until the point of first actuation of the MDI assembly 10. In this way, little to no power is drawn from the power supply until the first actuation of the MDI assembly 10, and it is thus possible to reduce or eliminate depletion of a power supply to the counting circuit 450 and to increase power supply longevity.

One example of such an arrangement is illustrated in the Figures. As illustrated, the actuator 50 is provided with a circuit activation projection or pin 54, which extends upwardly (with respect to the orientation of the device in FIG. 5) from the lower end wall 50*b* of actuator 50. As shown in FIG. 8, the circuit substrate 412 defines an exterior perimeter 414 and an aperture 418 which aligns with the aperture 238 in the housing portion 230. A battery contact 426 (FIGS. 9-11) is provided for connecting the battery 420 into the counting circuit 450.

As illustrated in FIG. 8, the electrical assembly 400 is positioned on the lower housing portion 230. Moreover, the housing portion 230 and the electrical assembly 400 are positioned in the actuator 50 such that the circuit activation projection or pin 54 aligns with the aperture 238 in the housing portion 230 and also aligns with the aperture 418 of the circuit substrate 412. In this configuration, when the counter 100 and the housing portion 230 are pressed in the downward direction as shown in FIGS. 6-7 during activation of the canister 20, the pin 54 extends through the apertures 238, 418. At times other than actuation, the pin 54 does not penetrate the apertures 238, 418.

Figure 9:
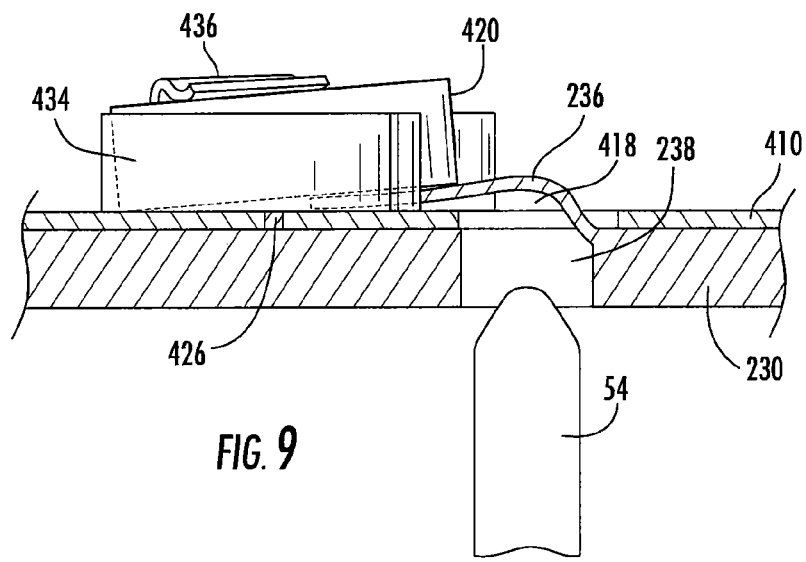
FIGS. 9-11 are cross sectional views of the electrical assembly and circuit activation pin of FIG. 8.

A further projection 236 is provided which extends from the lower housing portion 230 to the circuit substrate 412. The projection 236 overlies the aperture 418 and, in an initial configuration (prior to the first actuation of the MDI assembly 10), extends between the battery 420 and the battery contact 426, for example, as illustrated in FIGS. 8-9. The projection 236 is made from an electrically insulating material and thus prevents the flow of current from the battery 420 to the battery contact 426. That is, the projection 236 acts to keep the counting circuit open.

The projection 236 may be formed from a web of flexible material, such as a plastic film or sheet.

As noted above, on actuation of the MDI assembly 10, the pin 54 penetrates the aperture 238 of the lower housing portion 230 and the aperture 418 of the circuit substrate 412. Movement of the pin 54 through the apertures 238, 418 causes the pin 54 to contact and displace the projection 236. The projection 236 is displaced by the pin 54 to such an extent that it can no longer extend between the battery 420 and the battery contact 426. Electrical contact is thus made between the battery 420 and the battery contact 426. Withdrawal of the pin 54 from the apertures 238, 418 does not cause the projection 236 to re-take its original position and thus contact between the battery 420 and the battery contact 426 becomes permanent after the displacement of the projection 236.

Figure 10:
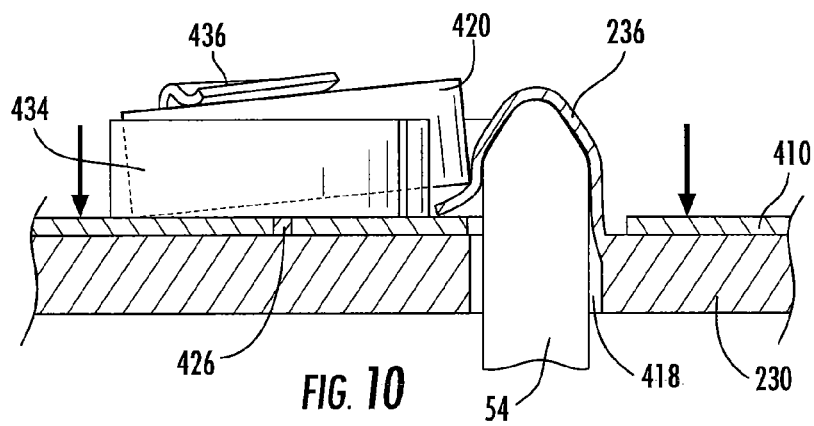
Figure 11:
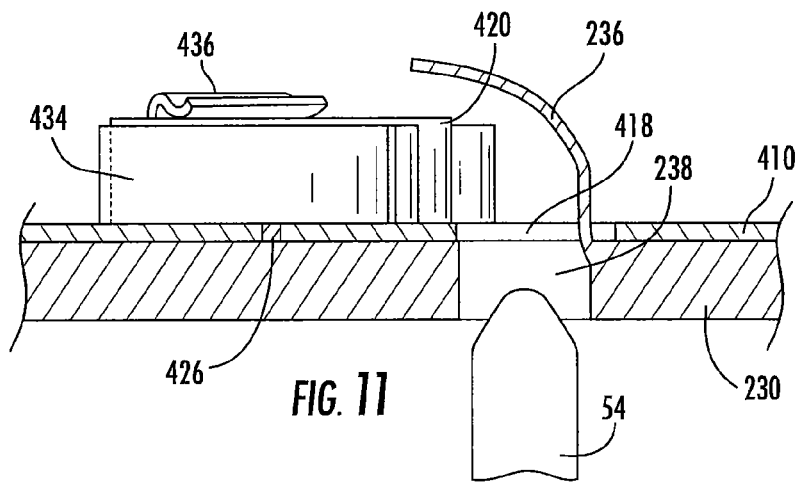

FIGS. 9-11 illustrate in more detail a particular embodiment of a power-conserving arrangement of the above type. As shown in FIGS. 9-11, in an initial at rest position (FIG. 9), the projection 236 is positioned underneath the battery 420 such that the battery 420 is tilted away from the battery contact 426. The projection 236 extends over the apertures 238, 418 in the rest position shown in FIG. 9. Accordingly, the projection 236 causes the battery 422 to remain out of the circuit 450 such that current does not flow through the circuit 450 and the power in the battery 420 is conserved prior to usage of the MDI assembly 10.

As illustrated in FIG. 10, as the housing 230 is pressed downward in the actuator 50 (FIGS. 5-7), the pin 54 extends through the apertures 238, 418 such that the pin 54 moves the projection 236 in a direction away from the battery 420. The battery 420 is held in position by a holder 434 that includes a biasing member 436. As illustrated in FIG. 11, the biasing member 436 of the battery holder 434 biases the battery 420 in the direction towards the substrate 410 and the battery contact 426. Thus, the battery 420 is positioned such that power flows to the battery contact 426, which in turn activates the counting circuit 450. As illustrated, the projection 236 remains free-floating in the counter housing 200 after the pin 54 has been pressed through the apertures 238, 418 to move the projection 236. After the initial activation as shown in FIGS. 9-10, the counting circuit 450 may index a counting value as described herein.

In this configuration, power consumption from the battery 420 may be reduced or eliminated before the first use of the MDI assembly 10, and the shelf life of the counter 100 may be increased.

Although embodiments according to the present invention are described with respect to the electrical assembly 400 and the battery tab 236 on the housing portion 230, it should be understood that other configurations may be used in which a tab or projection interrupts the electrical flow through a circuit prior to use. For example, the tab 236 may be provided on the circuit board 410 rather than as part of the housing portion 230. Moreover, although the tab 236 is illustrated as moving the battery 420 to a position that is spaced apart from the battery contact 426 in the circuit board 230, the tab 236 or other projection may be positioned in any suitable location on the circuit 450 so as to generally prevent current flow prior to use.

The power consumption by the electrical assembly 400 may be a factor in whether a sufficiently long service life of the dose counter can be achieved. Accordingly, in some embodiments, the display 430 may be a display having a reduced power consumption. For example, in some embodiments, the display 430 may be a display in which power is generally consumed for changing the display, and at other times the power consumption is negligible or nil.

For example, the display 430 may be an electrophoretic display, which may be referred to as an "electronic paper" or "electronic ink" display. Electrophoretic displays are commercially available from E Ink Corporation, Cambridge, Mass., USA., and use little or no power when a value on the display is in a static position. Electrophoretic displays may also be able to display characters (such a numerals indicating a remaining number of doses) particularly clearly and legibly.

Although electrophoretic displays may be used to conserve battery consumption and, consequently, to increase service life of the dose counter, it should be understood that any suitable display may be used, including other displays that are capable of minimizing power consumption.

In some embodiments, the initial value of counts that is stored in the counting circuit 450 may be set to account for a priming dose. For example, some metered-dose inhalers need to be primed in order to deliver a subsequent, accurate metered dose because the first dose(s) prior to priming may not be as accurately metered. In such a case, the initial value of the counts that is stored may be a negative number, or the counter may be configured not to display a remaining number of doses until after the priming steps have been completed. For such priming, the display 430 may be caused to display an alternative indication (other than a number of remaining doses) such as, for example, the letter "P".

In some embodiments, the counting circuit 450 is configured to analyze the signal from the actuation detection element 240 with respect to various parameters to determine if the said signal has a profile that indicates that a dose has likely been delivered. For example, when the actuation detection element is a piezoelectric or PVDF material, the magnitude of the charge resulting from the compression and/or deflection and/or deformation of the PVDF material on actuation of the MDI assembly 10 is related to the force applied by the user to the canister 20. Thus, the output of the actuation detection element 240 is a deflection charge profile which relates to the force applied to the canister 20 by the user. For brevity, this deflection charge profile, which is the actuation detection element output signal, may conveniently be referred to as an actuation sensor signal and may include a signal that provides an indication of compression and/or deflection and/or deformation of the PVDF material or other actuation detection element 240.

Figure 12:
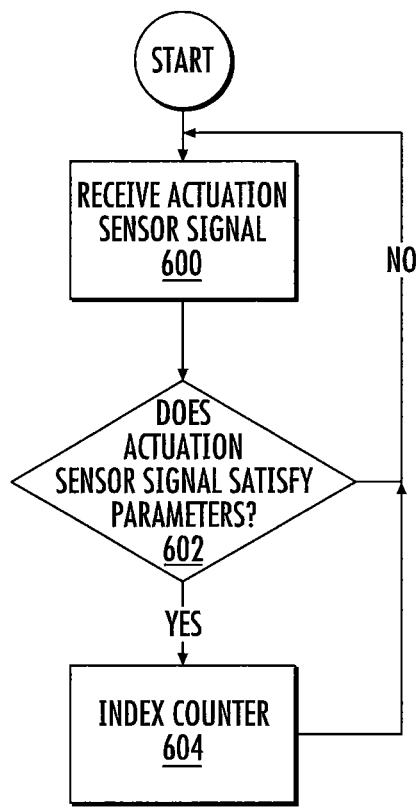
FIG. 12 is a flowchart illustrating operations according to some embodiments.

As shown in FIG. 12, the counting circuit 450 may receive an actuation signal (Block 600) from the actuation detection element 240 If the actuation signal satisfies one or more parameters (Block 602), then the counting circuit 450 indexes the counter (Block 604), e.g., by increasing or decreasing a counter value to indicate that an actuation of the MDI assembly 10 has occurred. If the actuation signal does not satisfy the parameters (Block 602), then the counting circuit 450 does not index the counter, and the counting circuit 450 waits for the next actuation signal.

For example, a previously unused metered-dose inhaler may have a counter circuit that has a starting value for the number of doses set at 402 (to account for 400 predetermined unit doses and two priming actuations). When the actuation signal satisfies one or more parameters, the counter is indexed by decreasing the starting value by 1, to 401, i.e. by one dose. Decreasing the counter at Block 604 may include changing a display value of the counter on the display 430 so that a user can easily determine how many doses are left in a canister. In some embodiments, the display

430 may include additional display elements for indicating that all of the doses in the canister 20 have been used, such as a change in color or a warning sign or symbol.

Figure 13:
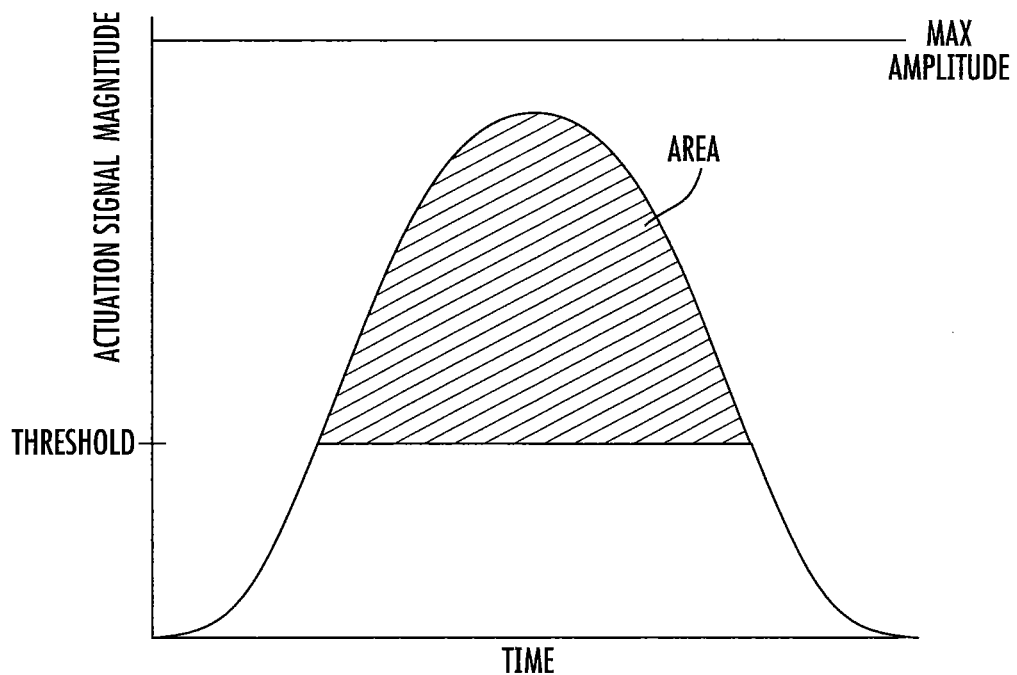
FIG. 13 is a graph of an exemplary force sensor signal from a force sensor indicating various parameters to determine whether the sensor signal indicates that a dose has been delivered.

The parameters of the actuation signal can include the magnitude and/or duration of the signal. For example, an exemplary actuation signal curve is shown in FIG. 13. In some embodiments as illustrated in FIG. 13, a threshold value is identified such that an actuation signal below the threshold is not counted by the counting circuit 450, i.e., the actuation signal below the threshold value does not satisfy the parameters to indicate a dose. The counting circuit 450 may be configured to identify an area of the actuation signal such as by calculating the average magnitude multiplied by the duration of an actuation signal above a threshold value or other analogous mathematical calculation. The counting circuit 450 may then register a dose count if the area of the actuation signal over the threshold is greater than a predetermined value. If the actuation signal curve does not reach a threshold value and/or does not reach the threshold value for a predetermined duration at a given amplitude, then the counter is not indexed. Also, in some embodiments, parameters used to determine whether a dose count should be registered may include a maximum amplitude. If the actuation signal curve exceeds the predetermined maximum amplitude threshold, and then the counter is not indexed. For example, the maximum amplitude threshold may indicate that the MDI assembly 10 has been dropped or otherwise moved in such a way that an actuation signal with a high magnitude is generated, but a dose is not delivered. The predetermined parameter values may be set by a user based on an initial dose or the predetermined value may be experimentally determined. The parameters that define an occurrence of a dose count may be stored in a memory of the counting circuit 450.

Although embodiments according to the invention are described with respect to determining an area or average magnitude multiplied by the duration of an actuation signal above a threshold value and, in some embodiments, below a maximum amplitude threshold value, it should be understood that any suitable parameter or set of parameters may be used to determine whether a dose has been delivered and the counter should be indexed or whether an actuation signal does not indicate dose delivery, such as when the inhaler assembly 10 is dropped or otherwise moved to generate a force signal when an actual dose is not administered. It should be noted, however, that in some embodiments, the counting circuit 450 may detect an activation based on a binary or "on-off" event. For example, as described herein, the actuation detection element 240 may be provided as a conductive material or layer applied to the inside of the housing 200 that mates with a corresponding conductive material or layer (such as the activation plate 310 or other conductive material or layer). When the conductive layers of the housing 200 and biasing element 300 contact one another, the counting circuit 450 is closed such that a current may flow through the counting circuit 450. In this configuration, activation of the canister 20 may be detected when the circuit 450 is closed without necessarily requiring an analysis of a force signal.

In some embodiments, dose counters described herein may be robust, resilient and/or resistant to false dose counts. In some embodiments, all the components of the dose counter may be contained within the actuator 50 such that all those counter components are protected from external interference, shock or damage. The counting of false doses may be reduced by using the same action (depression of the canister 20) for initiating the dose as for counting the dose and, in some embodiments, by assessing or analyzing the force applied to the canister (more specifically, the directly related force applied to the actuation detection element) and determining whether such force meets predefined criteria.

Dose counters according to some embodiments of the present invention can be made from relatively simple molded plastic parts and readily available electronic components, and can thus be manufactured at a price low enough to be acceptable to healthcare providers.

In some embodiments, the power consumption of the electronic assembly 400 may be reduced by minimizing the power consumption of the display 430. A service life of the counter power source may be increased. In some embodiments, increased service life of the counter may be achieved by reducing or eliminating power consumption form the power source (e.g., battery 420) prior to the first actuation of the MDI assembly 10.

The dose counter according to some embodiments can be used with known MDI canisters and/or MDI metering valves without modification of the canisters or metering valves. Market acceptance is the enhanced since there is no additional risk arising from new and un-tested canisters or valves.

In some embodiments, dose counters may be provided that may be adaptable to different valve and canister shapes. Moreover, dose counters according to some embodiments can be used with valves having different mechanical operational characteristics. For example, valves from different manufacturers may have different stroke lengths, the stroke length being the distance by which the valve stem must be depressed in order to dispense the metered dose. Counters according to some embodiments may utilize the movement of the biasing element 300 to close the gap 350 between the biasing element 300 and the actuation detection element 240, which may reduce or eliminate reliance on the extent of movement of a particular manufacturer's valve stem. For example, the actuation detection assembly 700 can be calibrated such that closure of the gap 350 occurs only in the final stages of travel of the valve stem on depression thereof, irrespective of the actual length traveled.

Dose counters according to some embodiments may be used with multiple MDI actuators while requiring minimal or no external modification to the MDI actuators. In some embodiments, the aperture 58 may be added to an existing MDI actuator. The "look and feel" of the MDI may thus be familiar to patients, which may help to achieve patient acceptance and compliance. In some embodiments, existing MDI actuators may be used with an internal modification to include the optional pin 54.

Dose counters according to some embodiments may not, in use, change or materially affect the mode of operation of the MDI with which the counter is used, because the patient is simply required to depress the canister into the actuator in the generally the same way as for known MDIs.

Further, the dose counters according to some embodiments may not, in use, materially change or adversely affect the force required to actuate the metered dose inhaler because the main resistance to depression of the canister into the actuator continues to be the biasing spring of the metering valve, as is the generally case with known inhalers. In some embodiments, any additional resistance attributable to the counter may be negligible. Accordingly, a patient may not perceive any difference in comparison with the MDI with which the patient is familiar, which may facilitate patient acceptance and compliance.

Dose counters according to some embodiments may not, even in the event of failure of the dose counter, prevent or affect safe and effective delivery of the dose by the metered dose inhaler. Even if the dose counter is not working, depression of the canister into the actuator may still result in the delivery of a dose from the metering valve (assuming that the formulation in the canister is not exhausted) since the movement of the valve stem on actuation may be independent of the operation of the counter.

In some embodiments, a permanent display, such as an electrophoretic display, may be used to display the counter value of the remaining doses for the associated metered dose inhaler. Accordingly, the remaining dose information may be displayed for a generally long period of time or even indefinitely instead of being displayed only for a limited time period, or only when the counter is "switched on."

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A dose counter for a metered dose inhaler having an activation valve at a valve end of the metered dose inhaler, the dose counter comprising:
  a housing having a first end and an opposing second end, the housing first end configured to receive a metered dose inhaler valve end, and the second end defining a cavity, the cavity comprising an upper wall portion directly adjacent the first end and an opposing lower wall portion distal to the first end that forms an at least partial closure of the cavity;
  an actuation detection assembly in the cavity of the housing, the actuation detection assembly comprising:
    an actuation detection element on the upper wall portion of the cavity on the second end of the housing; and
    an activation plate in the cavity of the housing, wherein the activation plate is configured to move between a first position in the cavity in which the activation plate is spaced apart from the actuation detection element on the housing by a gap and a second position in which the activation plate cooperates with the actuation detection element so that the actuation detection element generates an actuation signal.

2. The dose counter of claim 1, wherein the activation plate comprises a biasing element having one or more biasing members that are configured to bias the activation plate in the first position that is spaced apart from the actuation detection element.

3. The dose counter of claim 1, wherein the housing comprises a wall defining an aperture that is configured to receive an upper wall housing portion of the metered dose inhaler that cooperates with the activation plate to move the activation plate between the first and second position.

4. The dose counter of claim 1, wherein the housing is configured to be positioned together with a metered dose inhaler in an actuator body such that when the metered dose inhaler is pressed toward a base of the actuator body, a portion of the actuator body is moved toward the activation plate and moves the activation plate from the first position to the second position.

5. The dose counter of claim 4, wherein the portion of the actuator body that moves the activation plate from the first position to the second position comprises a sleeve configured to receive the activation valve of the metered dose inhaler.

6. The dose counter of claim 1, further comprising a counter circuit positioned in the cavity, the counter circuit being configured to receive an actuation signal from the actuation detection element and to index a counter value responsive to the actuation signal.

7. The dose counter of claim 6, wherein the counter circuit comprises a power supply, and the dose counter further comprising a projection in the housing that is configured to move between a first position in which the projection opens the counter circuit and a second position in which the projection allows the circuit to be closed so as to permit current flow from the power supply to activate the counter circuit.

8. The dose counter of claim 7, wherein the housing is configured to be positioned together with a metered dose inhaler in an actuator body, the metered dose inhaler having an actuation valve for delivering a metered dose from the metered dose inhaler when the metered dose inhaler is pressed toward a base of the actuator body, the actuator body comprising the circuit activation pin thereon such that, when the metered dose inhaler is pressed toward the base of the actuator body, the circuit activation pin passes through an aperture of the housing and moves the projection from the first position to the second position.

9. The dose counter of claim 7, wherein the counter circuit comprises a circuit board having a power supply contact thereon, and the projection is positioned between the circuit board and the power supply in the first position such that the projection moves the power supply away from the power supply contact to thereby open the circuit.

10. The dose counter of claim 9, further comprising a biasing unit that is configured to bias the power supply in a direction toward the power supply contact such that when the projection moves to the second position, the power supply moves in the direction toward the power supply contact and the power supply closes the circuit to permit current flow.

11. The dose counter of claim 6, wherein the counter circuit is configured to determine whether the actuation signal satisfies one or more dose delivery parameters and to index the counter value if the one or more dose delivery parameters are satisfied.

12. The dose counter of claim 11, wherein the actuation signal comprises a force profile curve and the dose delivery parameters comprise an area of the force profile curve that is above a threshold value.

13. The dose counter of claim 6, further comprising an electrophoretic display mounted on the housing, wherein the counter value is displayed on the electrophoretic display.

14. The dose counter of claim 2, wherein the biasing element comprises a generally planar base, and the one or more biasing members extend away from the base and are configured to abut a portion of the housing to thereby bias the biasing element in the first position.

15. The dose counter of claim 14, wherein the one or more biasing members extend at an obtuse angle away from the base.

16. The dose counter of claim 14, wherein the biasing element rests directly or indirectly on, but is not fixedly attached to, other portions of the dose counter.

17. The dose counter of claim 14, wherein the biasing element comprises the activation plate configured to contact the actuation detection element in the second position.

18. The dose counter of claim 1, wherein the actuation detection element is mounted on portion of the housing having a surface variation that is configured to increase a deflection of the actuation detection element in the second position.

19. The dose counter of claim 1, wherein the actuation detection element comprises a PVDF film.

20. The dose counter of claim 1, wherein the housing first end comprises one or more brackets configured for mounting the housing on a metered dose inhaler valve end.

21. The dose counter of claim 2, wherein the activation plate and the actuation detection element comprise a conductive material.

22. The dose counter of claim 21, further comprising a counter circuit positioned in the cavity, the counter circuit being configured to receive an actuation signal from the actuation detection element and to index a counter value responsive to the actuation signal, wherein the actuation signal is received when the conductive material of the activation plate contacts the conductive material of the actuation detection element to close the counter circuit.

23. The dose counter of claim 21, wherein the conductive material comprises a carbon or nickel layer.

24. A metered-dose inhaler assembly comprising:
a canister having a base end and a valve end opposite to the base end, the canister comprising an activation valve on the valve end thereof;
an actuator body having a canister receiving end and a dose dispensing end, the canister receiving end having an opening for receiving the canister therein and the dose dispensing end having an opening for dispensing a therapeutic agent from the canister;
a dose counter comprising:
a housing having a first end and an opposing second end, the housing first end configured to receive the canister at the valve end thereof, and the second end defining a cavity, the cavity comprising an upper wall portion directly adjacent the first end and an opposing lower wall portion distal to the first end that forms an at least partial closure of the cavity;
an actuation detection element on the upper wall portion of the cavity on the second end of the housing; and
an activation plate in the cavity of the housing, wherein the activation plate is configured to move between a first position in the cavity in which the activation plate is spaced apart from the actuation 'detection element on the housing by a gap and a second position in which the activation plate cooperates with the actuation detection element so that the actuation detection element generates an actuation signal; the actuator body comprising a cooperating element configured such that when the canister is moved relative to the actuator body from a rest position to a dispensing position, the cooperating element moves the activation plate from the first position to the second position.

* * * * *